United States Patent [19]

Maguer et al.

[11] 4,065,748

[45] Dec. 27, 1977

[54] TRANSMITTING AND RECEIVING MULTIPATH SONAR ANTENNA UTILIZING A SINGLE ACOUSTIC LENS

[75] Inventors: Pierre Maguer, Le Relecq-Kerhuon; Jean Verveur, Plouzane, both of France

[73] Assignee: Etat Francais represente par le Delegue Ministeriel pour l'Armement, Paris, France

[21] Appl. No.: 697,994

[22] Filed: June 21, 1976

[30] Foreign Application Priority Data

June 20, 1975 France .................. 75.20203

[51] Int. Cl.$^2$ ........................................ H04B 13/00
[52] U.S. Cl. ........................ 340/9; 340/3 A; 340/8 R; 340/8 L
[58] Field of Search .................. 340/3 A, 8 R, 8 MM, 340/8 LF, 8 L, 8 PC, 9, 10, 11, 12, 13

[56] References Cited

U.S. PATENT DOCUMENTS

| 2,961,636 | 11/1960 | Benecke | 340/9 X |
| 2,991,562 | 7/1961 | Hare | 340/9 UX |
| 3,483,504 | 12/1969 | Folds et al. | 340/8 L |
| 3,505,639 | 4/1970 | Chervenak et al. | 340/9 |
| 3,609,673 | 9/1971 | Muller | 340/3 A |
| 3,775,734 | 11/1973 | Bealor, Jr. | 340/8 L |
| 3,928,839 | 12/1975 | Warner et al. | 340/8 L |
| 3,949,349 | 4/1976 | Massa et al. | 340/9 |

*Primary Examiner*—Harold Tudor
*Attorney, Agent, or Firm*—Larson, Taylor and Hinds

[57] ABSTRACT

A simultaneously transmitting and receiving multipath sonar antenna comprises an acoustic lens which focuses received acoustic beams on a focal surface, and at least two intercalated groups of piezoelectric transducers disposed on the focal surface of the lens. The transducers of the at least two groups are tuned to different frequencies, and the transducers of each group are excited with a phase difference between one column and the next column of the same group.

5 Claims, 3 Drawing Figures

TRANSMITTING AND RECEIVING MULTIPATH SONAR ANTENNA UTILIZING A SINGLE ACOUSTIC LENS

FIELD OF THE INVENTION

The present invention relates generally to sonar systems, and more particular to multipath sonar antennas.

DESCRIPTION OF THE PRIOR ART

Conventional underwater acoustic multipath sonars used to detect or identify submerged objects basically comprise an antenna for emitting very short acoustic pulses, and an antenna for receiving echos transmitted or reflected by the sea bed and by submerged objects. These antennas are generally composed of vertical rows of piezoelectric transducers, the height of which determines the opening or size of the associated acoustic diaphragm.

Normally, conventional receiving antennas comprise rows of hydrophones which are connected to electronic devices that allow reception paths or beams to be formed in various bearings or directions by combining the signals produced by several rows of hydrophones after they have been dephased and weighted in amplitude. In order to improve the resulting power in a bearing or direction, it is known to focus the acoustic beams emitted by transmitting antenna of this type by electronically introducing a phase weighting equivalent to a characteristic curve of the antenna.

Acoustic lenses which comprise an enclosure filled with a liquid having a specific refractive index, such that the acoustic beams are focused on a focal surface, have also been used in conventional receiving antennas. A lens of this type generally comprises a cylindrical enclosure of relatively large diameter (approximately one meter), and upper and lower side plates which complete the lens. The hydrophones are disposed in vertical columns on the curved focal surface situated along the real wall of the lens. Each column of hydrophones corresponds to one reception path. A lens-type receiving antenna has the following advantages in relation to other conventional antennas. Such an antenna directly produces completely formed reception paths in the desired bearings or directions over the whole field of aperture of the antenna, for example, over a field of 60°. All of the reception paths are simultaneously and individually available, in parallel, without a specific electronic circuit for path formation, and this offers great flexibility in the choice of the covered field. The formation time of the reception lobes or beams is nil since the plane waves received, whatever their direction, are focused at the focus of the lens corresponding to the location of the associated hydrophones. The reception paths are therefore formed without the introduction of any additional electrical noise. The gain in sensitivity in the reception, as measured at the output of the transducers, is approximately 20 dB. The accoustic lenses are further characterized by the absence of image lobes.

Until now, however, although acoustic lenses have been used in receiving antennas to great advantage, it has not been possible to use the same acoustic lens as part of a simultaneously emitting and receiving antenna for a multipath sonar.

SUMMARY OF THE INVENTION

The object of the present invention is to provide a simultaneously emitting and receiving multipath sonar antenna which utilizes a common acoustic lens. A multipath sonar antenna constructed according to the present invention comprises, in combination, a conventional acoustic lens, wherein a cylindrical enclosure filled with a fluid focuses received acoustic beams on a focal surface, and at least two intercalated groups of columns of piezoelectric transducers disposed on the focal surface of the lens, the transducers of the at least two groups being tuned to the different frequencies.

In accordance with an important aspect of the invention, the transducers of a common group are excited at the same frequency, with a phase difference between one column and the next column of the same group, in order to spatially stagger the lobes or beams of emission and reception.

In accordance with a further aspect of the invention, the antenna comprises $2n$ columns, where n is an integer, and alternate columns constitute a first group of $n$ columns, the transducers of which are tuned to a frequency $F_1$, and the remaining columns constitute a second group of $n$ columns, the transducers of which are tuned to a second frequency $F_2$, different from frequency $F_1$. In each group, the transducers in adjacent or successive columns are preferably excited in phase opposition with respect to each other.

According to yet another feature of the present invention, which reduces the total power required to excite the transducers, as well as saturation of the sound level caused by non-linear acoustic occurances, the $2n$ columns of transducers are grouped into $p$ adjacent sections of $2n$ divided by p successive columns, where $p$ is in integer greater than one, such that the transducers of each section are excited simultaneously and the sections of transducers are excited sequentially (in time).

An important advantage of an antenna constructed according to the invention, and having a vertical axis, is that emission and reception are highly directional, and the resultant lobe or beam is the product of the emission and reception directionalities. Further, the maximum level of the secondary signal lobes or side beams in relation to the maximum level of the principal lobe or beam is quite low. It will be recalled that the directionality of an antenna is a function of the angular aperture of the principal lobe, which is twice the angle $\theta_3$ inside which the reduction in the level of the strength of the emission or reception signal in relation to the maximum level is less than 3 dB. Antenna directionality is also a function of a factor which is twice the angle $\theta_{10}$, the angle inside which the reduction in the level or the strength of the emission or reception signal in relation to the maximum is less than 10 dB. Measurements taken on an antenna constructed according to the invention indicate that, at transmission, principal lobes having an aperture $2\theta_3$ of approximately 1° and an angle corresponding to $2\theta_{10}$ of approximately 1.6° are obtained, as well as a maximum level of the first secondary lobe or side beam of approximately $-12$ dB in relation to the maximum level of the principal lobes. The measured curves of the emission-reception product indicate that a resultant principal lobe having an angle $2\theta_3$ of approximately 0.65° is obtained, which allows a considerable improvement in the discrimination power of the associated sonar. Although the maximum level of the first secondary lobes is approximately $-12$dB, the level continues to decrease constantly the greater the deviation from the axis of a reception path, to the point that when the deviation from a reception axis is greater than ±5°, the relative level of the secondary lobes is less than −26 dB. In prior art sonars, in contrast, the decrease in the maximum secondary lobes levels off at a floor of −18 dB, because of the interactions or couplings to the level of the formation circuits of the paths.

The greater reduction in the maximum level of the secondary lobes possible with the present invention allows an appreciable improvement in the contrast between the image of the sea bed and the image of a submerged object which is obtained. These results are due on the one hand to the fact that the adjoining emission and reception paths are not tuned to a common frequency, which suppresses occurrences of cross talk between neighboring paths. On the other hand, the excitation of successive transducers, which are tuned to the same frequency, in phase opposition causes the directionality lobes to be brought back at emission in the direction of the receiving beams and allows directivity lobes to add on each path at emission and at reception.

Other features and advantages of the invention will be set forth in, or apparent from, the detailed description of the preferred embodiments found hereinbelow.

DETAILED DESCRIPTION OF A PREFERRED EMBODIMENT

Figure 1:
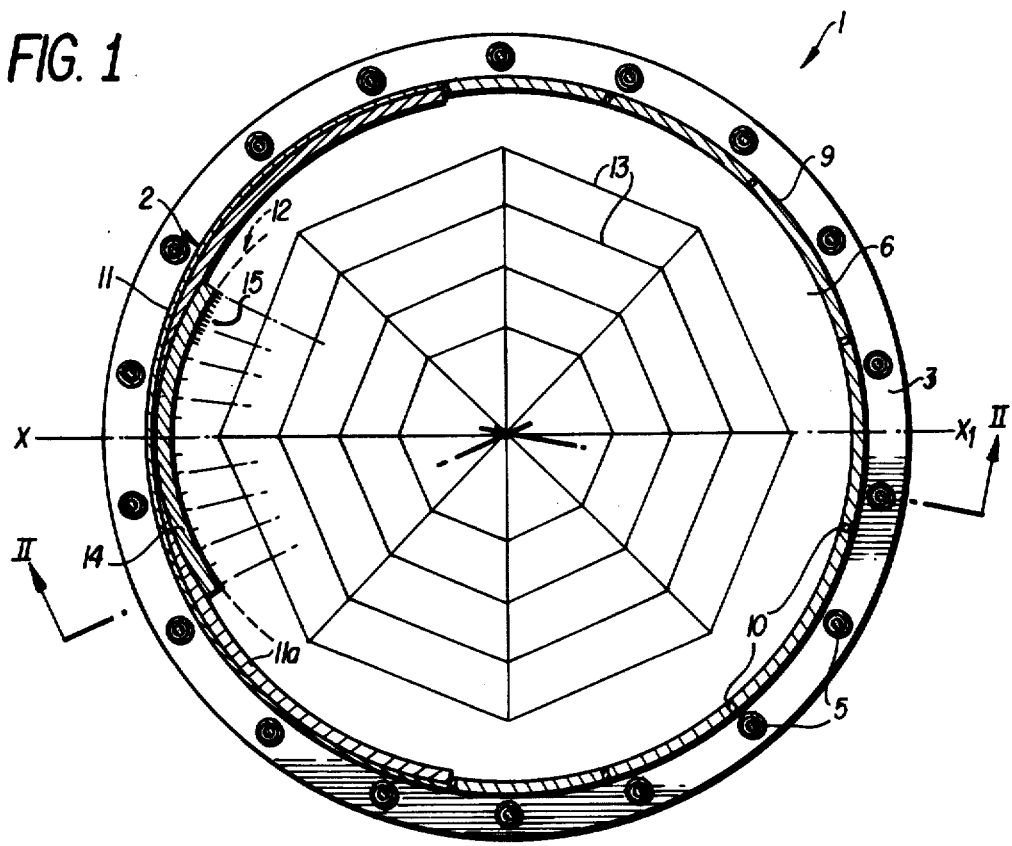
FIG. 1 is a horizontal or transverse section of an antenna constructed according to the invention taken generally along the line I—I of FIG. 2.
Figure 2:
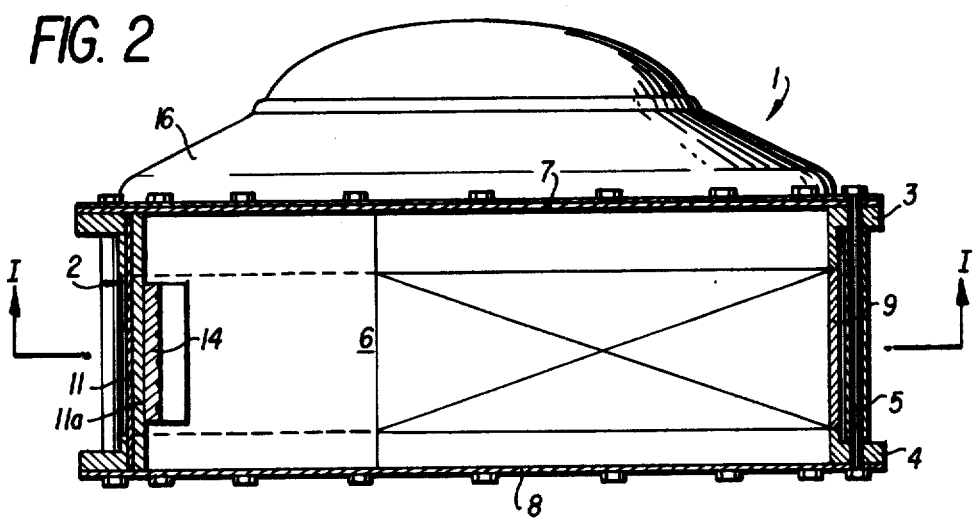
FIG. 2 is a vertical section taken generally along the line II—II of FIG. 1.

FIG. 1 represents an antenna constructed according to the invention which is generally designated by the reference numeral 1. Antenna 1 comprises a cylindrical case or housing 2 of a non-corroding metal such as aluminum bronze. Housing 2 comprises two holding or support members 3 and 4 connected to each other by tie rods 5 and cross pieces (not shown). Antenna 1 further comprises a careenage 16 in the form of an elliptical dome mounted on top of case 2. Careenage 16 houses the electronic circuitry associated with antenna 1.

Housing 2 encloses an essentially cylindrical, acoustic lens 6, which has a vertical axis and is defined by upper and lower planar side plates 7 and 8, respectively, attached to holder members 3 and 4. The operating diameter of the lens is, as an example, 0.80 m. The front of the lens 6 is comprised of an acoustically transparent material defining an aperture 9, which occupies an angular sector of 200°, with an axis of symmetry $X-X_1$. Aperture 9 constitutes the transmitting face of antenna 1, and the height thereof determines the opening in situ. The mechanical strength of aperture 9 is ensured by vertical cross pieces 10 embedded, at the time of moulding, in the material comprising the front of lens 6. Lens 6 is defined at its upper and lower parts by the two side plates 7 and 8, in front by the aperture 9, and in the rear by a wall 11 which occupies the space defined between the two moulding members 3 and 4 and between the two ends of aperture 9. Wall 11 is lined with an acoustically absorbant layer 11a.

Lens 6 is filled with a suitable liquid, such as a mixture of freons, whose acoustic impedance is such that when received acoustic beams break the contact surface between the liquid and aperture 9, they are so refracted that all the acoustic beams parallel to one particular direction converge on substantially one vertically-oriented focal line situated in the liquid. Together the various focal lines thus formed constitute a cylindrical focal surface 12, having as an axis of symmetry the axis $X-X_1$. By varying the proportions of the mixture used to fill lens 6, the refractive index of the liquid can be varied, and the lens focused to a predetermined distance, and adjusted to obtain the desired depth of field, which may vary, for example, from 10 to 1,000 m.

The internal surfaces of upper and lower side plates 7 and 8 are covered by a layer of acoustically reflective material, such as, for example, Klegecell, which is a cellular material of a resin capable of being polymerized, and which constitutes an air reflector. This layer serves to guide the acoustic waves without phase inversion, which prevents the lobe in situ from being disturbed. The internal faces of side plates 7 and 8 are also provided with elements 13, which, as shown in FIG. 1, form a polygonal network in cobweb-form. Heating elements 13, having a total capacity on the order of Kilowatts, serve to stabilize the temperature of the fluid filling lens 6 at a value compatible with the temperature of the external environment.

Antenna 1 further comprises, at the rear of lens 6, a unit transducer 14, concave in the direction of emission (reception), and having an angle, at the center, of 60°. Unit 14 bears 64 vertical columns 15 of ceramic piezoelectric transducers which are disposed on the focal surface 12, and in the liquid, of lens 6. The transducers of columns 15 serve to successively emit very short acoustic pulses, and to detect echos of the pulses reflected back by the sea bottom and submerged objects in various directions. Associated with each column 15 is one receiving path, which path also passes through the center of lens 6. By way of a non-limiting numerical example, the height of each column 15 is 50 mm, the space between columns is 4.75 mm and the width of the transducers is 4.4 mm. Each column 15 is connected to a preamplifier.

Considering the columns 15 as numbered in sequence from 1 to 64, starting from one end, the columns constitute two groups: that of the odd columns 1, 3, 5 . . . 63; and that of the even columns 2, 4 . . . 64. According to one aspect of the invention, the transducers of the even columns are tuned to a frequency $F_1$ and the transducers of the odd columns are tuned to a frequency $F_2$. At emission the transducers are obivously excited at their tuning frequency. For example, the transducers of the 32 even columns are tuned on a frequency of approximately 140 KHZ, while the transducers of the 32 odd columns are tuned on a frequency of approximately 160 KHZ. The fact that two adjoining paths are not tuned on the same frequency avoids the occurrence of cross talk between neighboring paths, and therefore allows paths to be used in close proximity while gaining maximum benefit from the fineness of these paths, which results in a better resolving power.

According to another feature of the invention, the transducers of successive columns of a common group, which are tuned to a common frequency, are excited, at emission, in phase opposition from one column to the next column of the same group. For example, the transducers of columns 1, 5, 9 etc., on the one hand, and the transducers of the columns 3, 7, 11, etc, on the other hand, are excited in phase opposition. The fact that the excitation provided is in phase opposition means that the emission and reception lobes of each path are in the same direction. Otherwise, the emission lobe of two neighboring paths, excited simultaneously, would be located along the middle axis between these two paths.

The power necessary for exciting the transducer of each column is approximately 100 watts. In order to reduce the power necessary to excite the transducers, as well as saturation of the sound level caused by non-linear acoustic occurrences, the columns 15 are grouped into several sections, for example into eight sections S1 to S8, each comprising eight columns. The transducers of each section are excited simultaneously, and the sections are excited sequentially in time in order to scan the entire angular field.

The numerical parameters of an antenna constructed according to the invention are, for example, the following:

Duration of each acoustic emission pulse: 120 µs or 500 µs.
Sensitivity at reception $Sh = -72$ dB.
Sound level in each path $Ns \geq 110$ dB.
Weight: 300 Kgs.
Width of path in bearing: 0.650.
Level of the highest secondary lobe: $-12$ dB.

Another of the principal advantages of an antenna constructed according to the present invention concerns the fact that the paths are formed by a lens and therefore the formation of the directionality lobes is immediate. Therefore, very short pulses may be used, having a duration of 120 µs which improves the resolving power in distance.

Further, the directionality diagram of the antenna is characterised by a very marked, progressive drop in the level of the secondary lobes, these lobes being practically non-existent for angular deflections higher than $\pm 5°$ from the direction of each path. In existing sonars, on the other hand, the level of the secondary lobes remains constant at approximately $-18$ dB over the whole unsounded section (i.e., that section not being subjected to acoustic radiation). Since the secondary lobes cause a reduction in the contrast of the echos received, a sonar constructed according to the invention gives highly contrasted and more easily identifiable images of submerged objects. The improvement in the contrast is approximately 6 to 10 dB.

Figure 3:
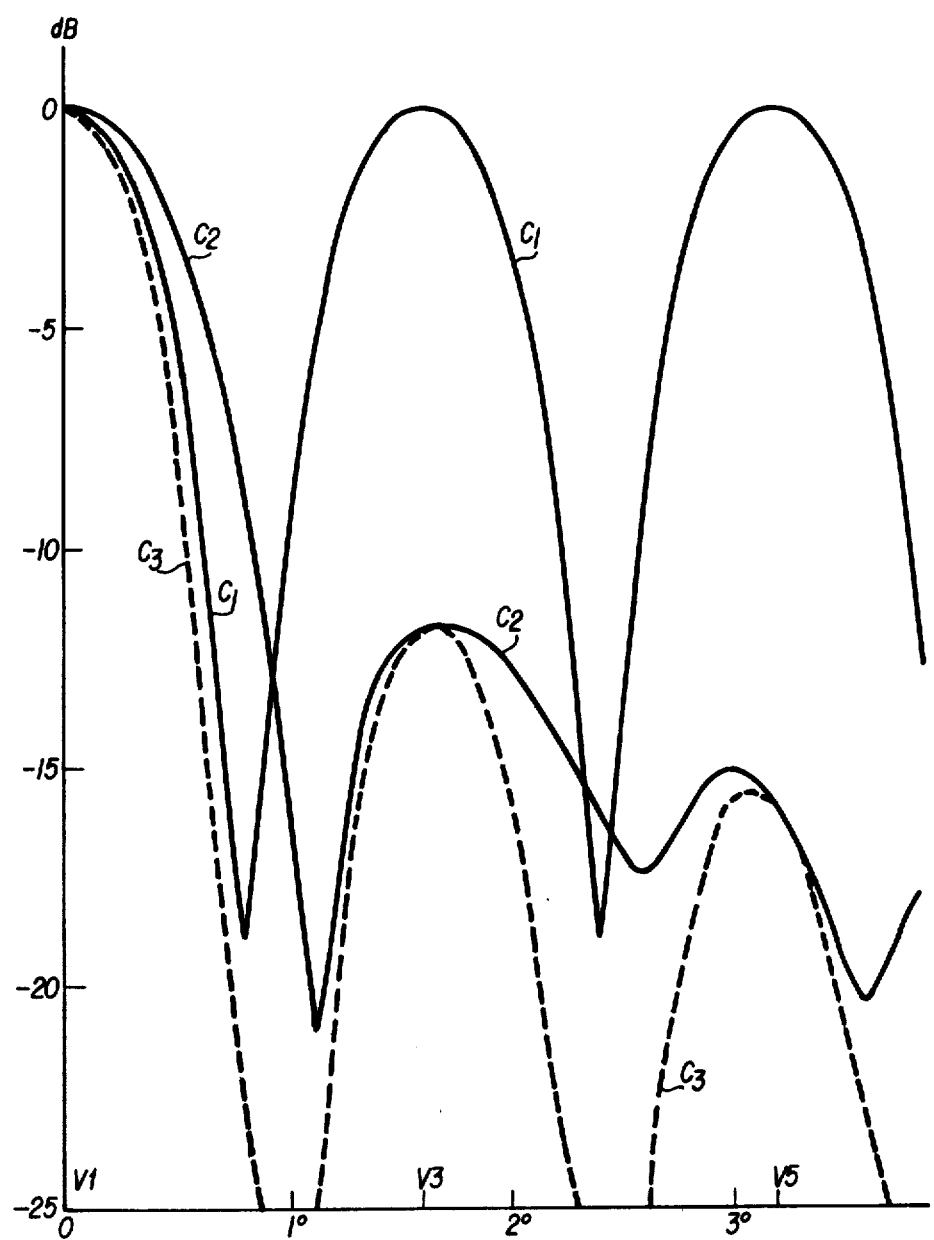
FIG. 3 is a graphical representation showing the relationships among the directionality lobes of the antenna shown in FIGS. 1 and 2.

There is shown, as an example, in FIG. 3 a graph of the directionality lobes which have been measured for an antenna in which the angular space between adjoining paths is 0.8°. The angular variations in degrees in relation to the bearing of a path, for example path $V_1$, are shown along the abscissa. The levels of the signal strength in dB in relation to the maximum level along the axis of a path are shown along the ordinate. The curve $C_1$ represents the directionality lobes at emission. The curve $C_1$ shows staggered maximums of 1.6° corresponding to the odd paths $V_1$, $V_3$, $V_5$ which are excited on a common frequency $F_1$. Of course, the directionality of lobes of even paths which are excited on a different frequency do not appear. The curve $C_2$ represents the directionality lobes at reception from the path $V_1$. The curve in dashed lines $C_3$ represents the directionality lobes resulting from the path $V_1$ which are the product of the lobes at emission and at reception. It can be seen that the aperture $2\theta_3$ of the resultant lobe is approximately 0.65°. The maximum level of the secondary lobes is $-12$ dB for the first and $-15$ dB for the second and decreases regularly as the distance away from the axis of the path is increased. Outside a section of $\pm 5°$ on both sides of the axis of the path, the maximum level of the secondary lobes is less than $-26$ dB.

It will be appreciated by those skilled in the art that although the invention has been described relative to exemplary embodiments thereof, modifications and variations can be effected in these embodiments without departing from the scope and spirit of the invention.

We claim:

1. A multipath, emitting and receiving sonar antenna comprising, in combination, an acoustic lens comprising a cylindrical enclosure filled with a fluid which focuses received acoustic beams on a focal surface, and at least two intercalated groups of columns of piezoelectric transducers placed on said focal surface, wherein the transducers of each of said at least two groups are tuned to a different frequency with respect to the other said group, and the transducers of a common group are excited on the same frequency, with the transducers of one column differing in phase with respect to the next column of the same group.

2. The antenna of claim 1, comprising $2n$ columns of transducers, where $n$ is an integer, and alternate columns constitute a first group of $n$ columns, the transducers of which are tuned to a first frequency, and the remaining columns constitute a second group of $n$ columns, the transducers of which are tuned to a second frequency different from said first frequency, and the transducers of each group are excited such that the transducers in adjacent or successive columns are excited in phase opposition with respect to each other.

3. The antenna of claim 2 wherein the $2n$ columns of transducers are grouped into p adjacent sections of $2n/p$ successive columns, where p is an integer greater than 1, such that the transducers of each section are excited simultaneously and the sections of transducers are excited sequentially.

4. The antenna of claim 1 wherein said lens is partially defined by two horizontal lower and upper side plates whose internal faces are covered by an acoustic air reflective layer.

5. The antenna of claim 4 wherein said side plates are provided with a network of heating elements on their internal faces.

* * * * *